US006891052B1

(12) United States Patent
Tanner et al.

(10) Patent No.: US 6,891,052 B1
(45) Date of Patent: May 10, 2005

(54) PROCESS FOR FORMING VINYL ESTER FROM CARBOXYLIC ACID WITH WATER TREATMENT OF THE REACTION MIXTURE

(75) Inventors: Ky I. Tanner, Baton Rouge, LA (US); Charles M. Yarbrough, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 08/963,569

(22) Filed: Oct. 31, 1997

(51) Int. Cl.[7] .................................................. C11C 3/00
(52) U.S. Cl. ........................................ 554/161; 554/124
(58) Field of Search ................................ 554/124, 161

(56) References Cited

U.S. PATENT DOCUMENTS

| 2,066,075 A | * 12/1936 | Reppe et al. |
| 3,285,941 A | 11/1966 | Engel et al. ............. 260/410.9 |
| 3,455,998 A | 7/1969 | Arpe |
| 3,527,779 A | 9/1970 | Paulis et al. ................. 260/413 |
| 3,607,915 A | 9/1971 | Borsboom et al. |

FOREIGN PATENT DOCUMENTS

DE             1237557 B      3/1963

* cited by examiner

Primary Examiner—Deborah D. Carr

(57) ABSTRACT

A process is disclosed for forming a vinyl ester from a carboxylic acid and acetylene in the presence of a zinc carboxylate catalyst, wherein a mixture of carboxylic acid and zinc carboxylate catalyst is formed and the water content of the mixture is reduced to between about 0.02 wt. % and about 0.3 wt. %, prior to introduction of the acetylene into the reactor. Optionally, water is introduced into the reactor during the reaction to hydrate any anhydride by-product of the reaction present in the reactor to carboxylic acid reactant. Water is added during the reaction in an amount that is sufficient to convert the anhydride by-product to carboxylic acid reactant, but does not raise the amount of water in the reaction mixture to a level that will reduce the reactivity of the catalyst or reduce the rate of the vinylation reaction.

16 Claims, 2 Drawing Sheets

PROCESS FOR FORMING VINYL ESTER FROM CARBOXYLIC ACID WITH WATER TREATMENT OF THE REACTION MIXTURE

The present invention relates generally to the production of a vinyl ester from a carboxylic acid and acetylene in the presence of a zinc carboxylate catalyst. In particular, the present invention relates to a process for forming a vinyl ester from a carboxylic acid in a reactor in which the carboxylic acid is mixed with the catalyst and the water content of the mixture is reduced prior to the introduction of acetylene into the reactor to increase the rate of reaction, but not to an extent that will increase the viscosity of the vinyl ester product.

BACKGROUND OF THE INVENTION

Vinyl esters (VE) are useful in the production of paints and as comonomers used to form adhesives. It is well known to form vinyl esters by reacting a carboxylic acid with acetylene according to the following reaction:

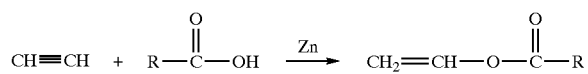

For example, this reaction is described in U.S. Pat. No. 1,786,647 to Dykstra et al. As a by-product, the reaction also produces an anhydride component primarily in accordance with the following reaction:

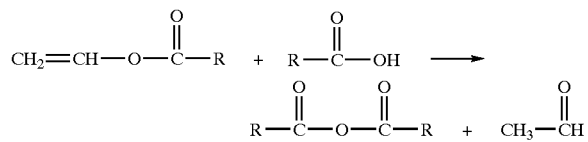

One particularly useful class of vinyl esters are esters of neo acids. In neo acids, the carboxylic acid group is attached to a hydrocarbon backbone through a tertiary carbon atom (a carbon atom that, is attached to three carbon atoms in addition to the carboxylic acid group). Such neo acids, described for example, in U.S. Pat. No. 3,527,779 to Paulis et al., are formed from olefin, carbon dioxide and water via Koch synthesis, and have the general formula:

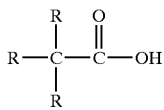

wherein R represents hydrocarbon groups.

The reaction of carboxylic acid and acetylene to form a corresponding vinyl ester is commonly performed in the presence of a zinc carboxylate catalyst. Such catalysts are formed by dissolving zinc oxide, zinc hydroxide or zinc carbonate in a carboxylic acid. (See U.S. Pat. No. 2,066,075 to Reppe). Over the years, a number of improvements to the basic reaction have been proposed. U.S. Pat. No. 3,285,941 to Engel et al. teaches that vinyl esters of carboxylic acids of $C_8$ to $C_{19}$ alkanes can be formed by passing a gaseous mixture of a vaporized higher carboxylic acids and acetylene into a heated, high boiling, inert liquid containing a dispersed catalyst, controlling conditions such that the concentration of carboxylic acid in the liquid phase is maintained below 5 wt. %, and subsequently separating the vinyl ester from the gaseous effluent of the liquid phase.

U.S. Pat. No. 3,455,998 suggests that the reaction of carboxylic acid and acetylene to form vinyl ester can be conducted more efficiently in the presence of both a zinc carboxylate catalyst and a metal-containing Lewis acid. A still further improvement to the conventional reaction is disclosed in U.S. Pat. No. 3,607,915 to Borsboom et al. which describes a continuous process for producing vinyl esters from carboxylic acid and acetylene, with improved efficiency, by contacting a catalyst-containing reaction recycle stream with at least a portion of the carboxylic acid to be vinylated, before the introduction of the carboxylic acid into the reaction zone of the reactor.

Because of increased demand and fierce competition between manufacturers, there has been a continued need for further improvements that allow for more efficient and lower cost production of vinyl esters from carboxylic acids. The present inventors have developed a novel process involving water treatment of the solution of catalyst, reactants, products and by-products that leads to a more rapid reaction and further lowers costs by converting reaction by-product back into a usable reactant component.

Other and further objects, advantages and features of the present invention will be understood by reference to the following specification.

SUMMARY OF THE INVENTION

A process is disclosed for forming a vinyl ester from a corresponding carboxylic acid and acetylene in the presence of a zinc carboxylate catalyst, wherein an initial mixture of carboxylic acid reactant and zinc carboxylate catalyst is formed and the level of water in the initial mixture is reduced to level within a range from about 0.05 to about 0.25 wt. %, based on the total weight of the mixture, prior to the introduction of the acetylene reactant into the reactor.

In another aspect of the present invention, water is introduced into the reactor during the reaction to convert an anhydride by-product of the reaction present in the reactor to carboxylic acid reactant by the following reaction:

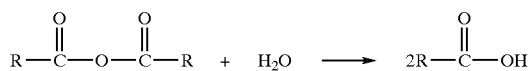

Water is added during the reaction in an amount that is sufficient to convert the anhydride by-product to carboxylic acid reactant, but not in an amount that raises the amount of water in the reaction mixture to a level that will reduce the reactivity of the catalyst or reduce the overall rate of the reaction.

The present inventors have discovered that when water is removed from the initial mixture of carboxylic acid reactant and zinc carboxylate catalyst prior to the introduction of the acetylene, the reaction progresses more rapidly, leading to a more efficient process. The addition of water thins the reaction mixture to provide for easier processing. However, when the amount of water in the initial mixture is decreased below a minimum weight percent (<about 0.02 wt. %) the viscosity of the resulting reaction mixture after stripping of the vinyl ester product is disadvantageously increased. The addition of water to the reaction mixture during the reaction, destroys the unwanted anhydride by-product of the reaction. Also, the conversion of the anhydride by-product to carboxylic acid provides a source of additional reactant, leading to an additional economic advantage.

DESCRIPTION OF THE PREFERRED EMBODIMENTS

Although the process of the present invention can be advantageously practiced with any carboxylic acids, the preferred carboxylic acid reactants are $C_9$ to $C_{13}$ neo acids, formed by reacting olefin, carbon dioxide and water in a Koch synthesis. Neo acids are carboxylic acids in which the carbon atom immediately adjacent to the carboxylic carbon is a tertiary alpha carbon (triple branched). The neo acid branches of a $C_n$ neo acid can extend anywhere from $C_1$ to $C_{n-4}$ in length and can be combined in numerous ways. Therefore, a CIO neo acid, for example, is not a pure compound, but rather a mixture of isomers having 10 total carbon atoms.

The catalyst is a metal salt of a carboxylic acid. Suitable metal salts are compounds of magnesium, iron, copper, aluminum, tin, boron, zinc and cadmium. Particularly preferred are zinc salts of carboxylic acid which can be formed by reacting, for example, zinc oxide, zinc hydroxide or zinc carbonate, with a carboxylic acid. Preferably, the carboxylic acid used to form the catalyst will be the same as the carboxylic acid to be vinylated. When other carboxylic acids are used to form the catalyst, the anion of the acid moiety of the catalyst may exchange, to some extent, with the anion moiety of the acid being vinylated, causing an impure vinyl ester product. The zinc carboxylate catalyst may be prepared prior to introduction into the reactor, or alternatively, the zinc salt can be allowed to form in vitro, in the initial reaction mixture.

Figure 1:
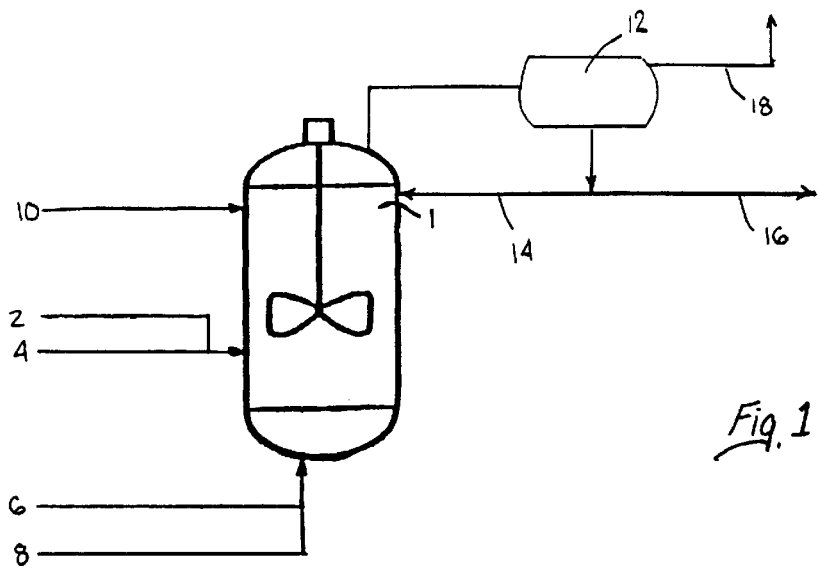
FIG. 1 is a schematic representation of the process according to a preferred embodiment of the present invention in a batch mode.

With reference to the batch reaction schematically represented by FIG. 1, an initial mixture is formed by mixing the neo acid from neo acid feed 2 with the zinc carboxylate catalyst from catalyst feed 4, to provide about a 1:25 to about a 1.5:1 weight ratio of catalyst solution to neo acid. A 1:1 ratio of catalyst solution to neo acid will provide about 8 wt. % catalyst, calculated as zinc, in the initial mixture. The initial mixture can be formed prior to introduction into, or in the reactor vessel 1, which has been purged of air prior to the introduction of the reaction mixture. When formed with conventional catalyst components, the resulting initial mixture will have a water content of about 0.6 wt. %.

Figure 3:
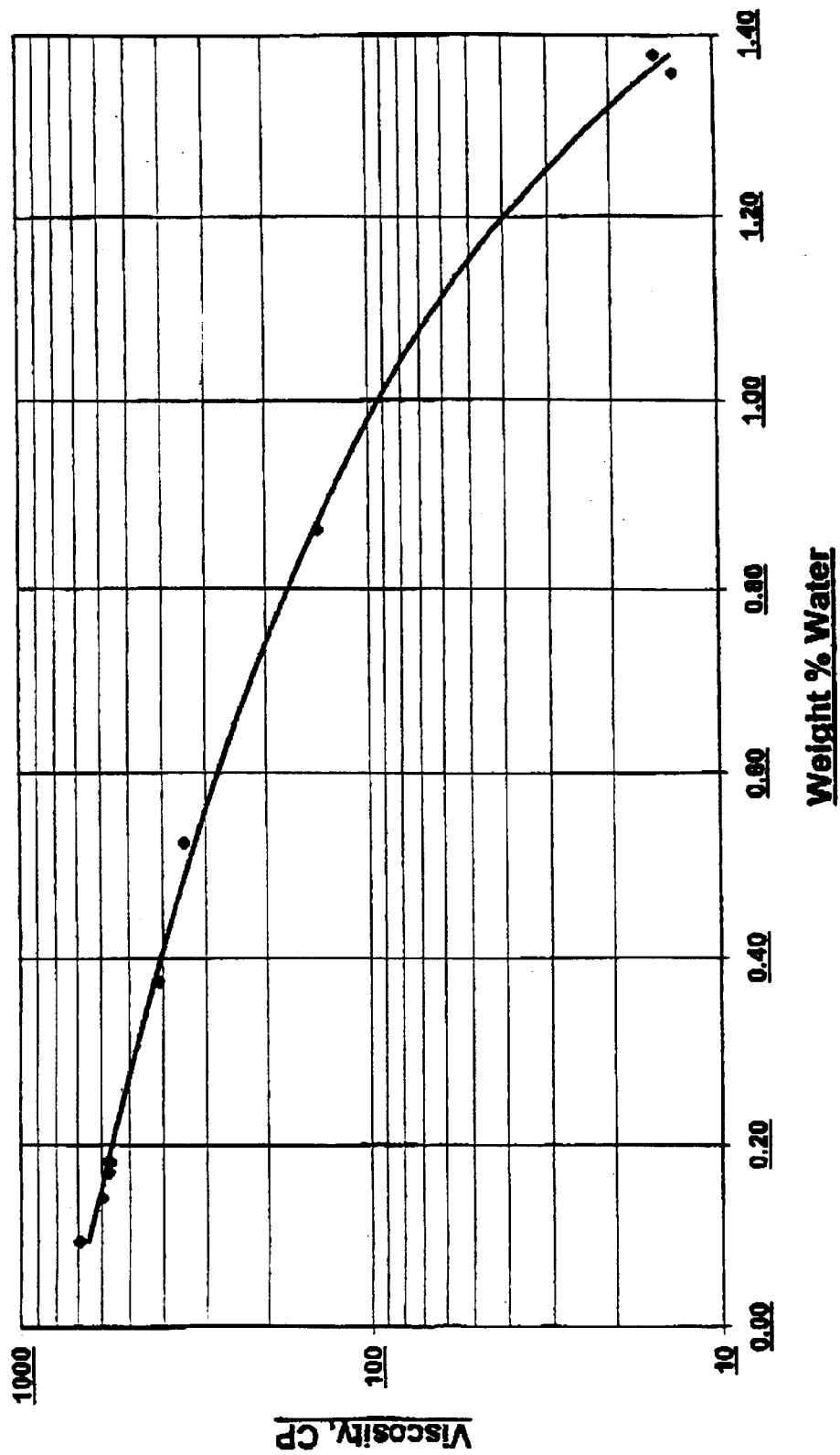
FIG. 3 is a graph plotting the water content of the reaction mixture versus viscosity.

The water content of the initial mixture is reduced to between about 0.02 and 0.3 wt. %, preferably between about 0.05 and 0.2 wt. %, most preferably between about 0.08 and about 0.15 wt. % prior to reaction with acetylene. When the water content of the initial mixture is decreased below 0.05 wt. %, the viscosity of the initial mixture and vinyl ester product becomes undesirable high, as shown in Table 1, and FIG. 3:

TABLE 1

WATER CONTENT OF ZINC NEODECANOATE REACTION MIXTURE VS. VISCOSITY (190° C.)

| Water Level | | Viscosity |
|---|---|---|
| ppm | wt. % | cps |
| 937 | 0.094 | 690 |
| 1420 | 0.142 | 594 |
| 1703 | 0.170 | 588 |
| 1818 | 0.182 | 576 |
| 1814 | 0.181 | 561 |
| 3744 | 0.374 | 410 |
| 5243 | 0.524 | 346 |
| 8649 | 0.865 | 140 |
| 13564 | 1.356 | 13.1 |
| 13770 | 1.377 | 14.8 |

Applicants have discovered that when the water content of the initial mixture is greater than 0.3 wt. %, the rate of reaction between the neo acid and acetylene is reduced. Water can be removed from the initial mixture by any suitable means. One particularly suitable method for reducing the water content of the initial mixture is by inert gas stripping at a high temperature. High temperature inert gas stripping of the initial mixture can be conducted either prior to the introduction of the initial mixture into the reactor vessel, or within the reactor vessel. For example, the initial mixture can be subjected to inert gas stripping with nitrogen, supplied through inert gas feed 6, at a temperature within the range of about 150° C. to about 200° C.

The vinylation reaction can be performed at atmospheric pressure or at reduced or elevated pressures. Under atmospheric pressure, the temperature of initial mixture is raised to a reaction temperature of about 150° C. to about 250° C., preferably about 180° C. to about 200° C. During the heating of the initial mixture, the reactor can be further purged with additional inert gas, e.g., nitrogen, to remove air and residual water vapor from the reactor vessel. Once the initial mixture reaches the reaction temperature, the source of purging nitrogen is cut out and acetylene reactant is introduced into the reactor vessel through acetylene feed 8, to initiate the vinylation reaction.

One by-product of the formation of a vinyl ester from a carboxylic acid and acetylene is anhydride, which is a result of the following side reaction:

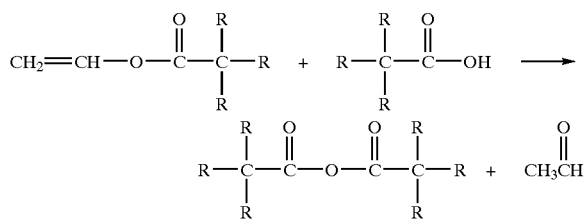

In another aspect of the present invention, water is added back into the reaction vessel through water feed 10 to convert the anhydride by-product into carboxylic acid reactant. The addition of water during the reaction provides two advantages, removal of an unwanted anhydride by-product from the reaction mixture, which will increase the reaction rate, and the supply of additional carboxylic acid reactant, which provides an economic benefit. The amount of water that is added to the reaction mixture during the vinylation reaction will be an amount of water that is sufficient to convert at least a portion of the anhydride byproduct to carboxylic acid, but will not raise the water content of the reaction mixture to a level that will adversely affect the reactivity of the catalyst (above 0.3 wt. %). The precise amount of water that can be added to the reaction mixture during the vinylation reaction will vary depending on a number of conditions (e.g., temperature, pressure, flow rate of reactants), but can be easily determined by one of ordinary skill by performance of a simple material balance calculation. Optionally, the water can also be added to the reaction mixture as steam.

Upon completion of the reaction, the vinyl ester product is separated from the catalyst and any remaining carboxylic acid reactant by conventional means. In a batch mode, such separating means can include, for example, a single stage stripping or vacuum flash. The vinyl ester products are more volatile than the neo acid from which it is formed. Therefore, separation of the vinyl ester product can be easily accomplished. The stripped product is condensed in a condensation drum 12. The condensation drum 12 is provided with reflux line 14, which allows for reflux of the crude product during the reaction. Upon completion of the reaction, product is removed from the condensation drum 12 through product line 16. The gas phase from the condensation drum is vented through vent line 18.

Figure 2:
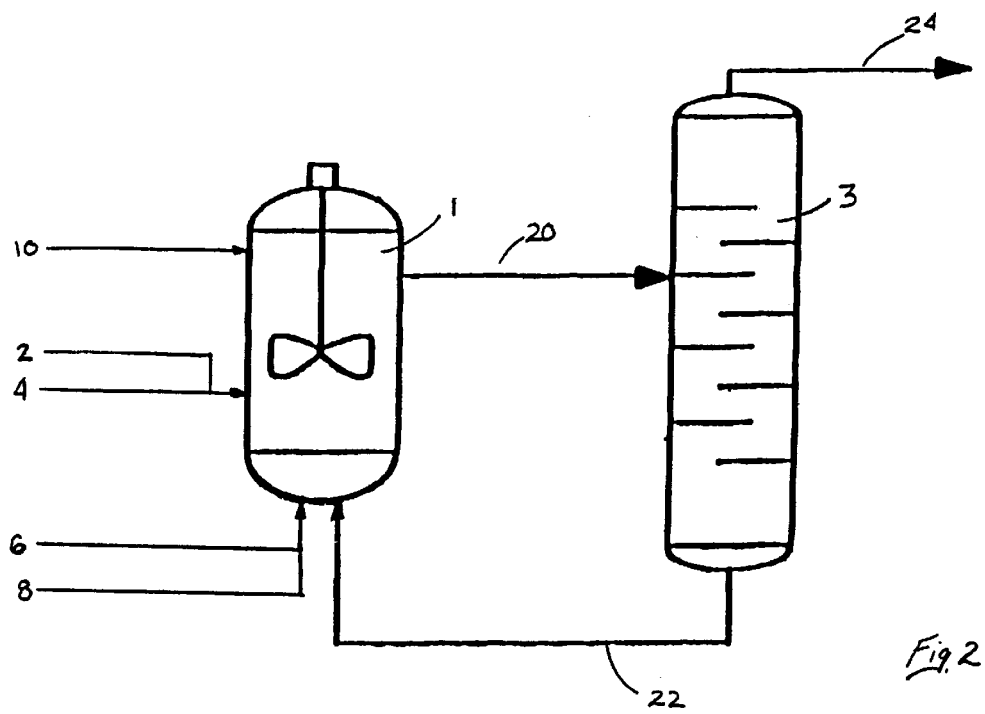
FIG. 2 is a schematic representation of the process according to a preferred embodiment of the present invention in a continuous mode.

In the continuous process of FIG. 2, crude product is removed from reactor 1 through crude product line 20 and passed to distillation column 3. Zinc carboxylates of neo acids are non-volatile viscous liquids at room temperature, and have the consistency of light mineral oils at operating temperatures. The zinc carboxylates of neo-acids are removed from distillation column 3 as bottoms and recycled to reactor vessel 1 through recycle line 22. Additional zinc catalyst can be provided to the reactor vessel to maintain a sufficient amount of catalyst upon introduction of the recycled bottoms. The more volatile vinyl ester product is removed as a light fraction from distillation column 3, through product line 24.

EXAMPLE 1

500 gram samples of reaction mixtures containing C10 Neo Acid and Zinc Neo-decanoate having varied water contents were reacted with 300 ml/min of acetylene in a batch reactor at 205° C. and 1 atm., with stirring (2" diameter stirrer rotating at 1750 rpm). The reaction rate of the sample reactions and water contents of the reaction mixtures are shown in Table 2. The data of Table 2 demonstrates that a decrease in the water content of the reaction mixture results in faster rates of reaction.

TABLE 2

| Initial $H_2O$ Content (wt. %) | Reaction Time (hrs.) | Final Vinyl Ester Solution Content (wt. %) |
|---|---|---|
| 0.60 | 4.00 | 11.8 |
| 0.20 | 2.50 | 49.1 |
| 0.15 | 2.25 | 45.7 |
| 0.05 | 1.50 | 43.8 |

EXAMPLE 2

The water content of a base reaction mixture (500 grams) containing 50 wt. % Zinc Neodecanoate, 25 wt. % Neo Acid and 25 wt. % anhydride at 205° C. was determined to be 0.03 wt. %. A second reaction mixture, identical to the base reaction mixture was prepared and 7 ml. of $H_2O$ was added thereto. Each of the base reaction mixture and the second reaction mixture were allowed to react for 15 minutes, at which time the amount of anhydride by-product was measured. A comparison of results is shown in Table 3, and demonstrates that addition of water to the reaction mixture, during the reaction, is effective in converting anhydride by-product to useful neo-acid reactant.

TABLE 3

| | wt. % $H_2O$ | wt. % Anhydride |
|---|---|---|
| (1) Base Mixture | 0.03 | 7.7 |
| (2) Base Mixture + 7 ml $H_2O$ | — | 0.1 |

It should be understood that the forgoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed:

1. A process for forming a vinyl ester from carboxylic acid and acetylene in the presence of a metal salt of carboxylic acid as catalyst, said process comprising the steps of:

charging said carboxylic acid and said catalyst to a reactor vessel to form an initial mixture;

maintaining the water content in said initial mixture at a level within a range between about 0.02 wt. % to about 0.3 wt. %, based on the total weight of said initial mixture; and reacting acetylene with said initial mixture of said carboxylic acid and said catalyst, thereby forming a vinyl ester product.

2. The process of claim 1, wherein said catalyst is zinc carboxylate.

3. The process of claim 1, wherein said water content is within a range between from about 0.05 wt. % to about 0.20 wt. %.

4. The process of claim 3, wherein said water content is within a range between from about 0.08 wt. % to about 0.15 wt. %.

5. The process of claim 1, wherein said carboxylic acid is a neo-acid.

6. The process of claim 5, wherein said neo-acid comprises from about 9 to about 13 total carbon atoms.

7. The process of claim 6, wherein said neo-acid is neo-decanoic acid.

8. The process of claim 1, where in an initial reaction mixture comprises a mixture of said zinc carboxylate catalyst and said carboxylic acid in a weight ratio in a range from about 1:25 to about 1.5:1.

9. The process of claim 8, wherein said ratio is about 1:1.

10. The process of claim 1 wherein said water content of said mixture is reduced by inert gas stripping.

11. The process of claim 10, wherein said inert gas stripping is performed using nitrogen at a temperature within a range from about 150° C. to about 250° C.

12. The process of claim 1, wherein said mixture is contacted with said acetylene at a temperature within a range from about 150° C. to about 250° C. and at about atmospheric pressure.

13. A process for forming a vinyl ester from carboxylic acid and acetylene in the presence of a metal salt of carboxylic acid as catalyst, said process comprising the steps of:

charging said carboxylic acid and said catalyst to a reactor vessel to form an initial mixture;

maintaining the water content in said initial mixture at a level within a range between about 0.02 wt. % to about 0.3 wt. %, based on the total weight of said initial mixture; and reacting acetylene with said initial mixture in the presence of water thereby forming a vinyl ester product wherein said water is introduced into said reactor vessel in an amount sufficient to convert said byproduct anhydride, but not reduce the activity of said zinc carboxylate catalyst or the rate of the esterification reaction.

14. The process of claim 1, wherein said caboxylic acid and said acetylene are reacted in a batch reaction at a temperature within a range from about 150° C. to about 250° C. and at about atmospheric pressure.

15. The process of claim 14, wherein said carboxylic acid and said acetylene are reacted at a temperature within a range from about 180° C. to about 200° C.

16. The process of claim 1, wherein said carboxylic acid and acetylene are reacted in a continues reaction at a temperature within a range from about 150° C. to about 250° C. and at about atmospheric pressure.

* * * * *